(12) United States Patent
Lytle et al.

(10) Patent No.: US 9,750,459 B2
(45) Date of Patent: Sep. 5, 2017

(54) IMAGING ALIGNMENT APPARATUS AND METHOD OF USE THEREFOR

(71) Applicants: Andrew B. Lytle, Farmington Hills, MI (US); James J. Verner, Beverly Hills, MI (US)

(72) Inventors: Andrew B. Lytle, Farmington Hills, MI (US); James J. Verner, Beverly Hills, MI (US)

( * ) Notice: Subject to any disclaimer, the term of this patent is extended or adjusted under 35 U.S.C. 154(b) by 875 days.

(21) Appl. No.: 14/068,852

(22) Filed: Oct. 31, 2013

(65) Prior Publication Data

US 2014/0128717 A1 May 8, 2014

Related U.S. Application Data

(60) Provisional application No. 61/722,471, filed on Nov. 5, 2012.

(51) Int. Cl.
*G06K 9/00* (2006.01)
*A61B 5/00* (2006.01)
(Continued)

(52) U.S. Cl.
CPC ............ *A61B 5/706* (2013.01); *A61B 5/6823* (2013.01); *A61B 6/04* (2013.01); *A61B 6/08* (2013.01);
(Continued)

(58) Field of Classification Search
CPC ...... A61B 2034/107; A61B 2090/3966; A61B 34/10; A61B 6/032; A61B 17/8066; A61B 2090/376; A61B 34/20; A61B 6/485; A61B 6/487; A61B 2034/108; A61B 6/547; G06T 7/0012; G06T 2207/30008; G06T 2207/10116; G06T 2207/10081;
(Continued)

(56) References Cited

U.S. PATENT DOCUMENTS 8,611,504 B2 12/2013 Kubiak et al.
2009/0226060 A1* 9/2009 Gering .................. G06T 7/0081
382/128

(Continued)

OTHER PUBLICATIONS

Ahmad et al., Proper positioning for the pelvis and proximal femur, Aug. 2003, auntminnie.com, white papers on radiologic patient positioning techniques for xray examinations, No. 16th, pp. 1-10.*

(Continued)

*Primary Examiner* — Vu Le
*Assistant Examiner* — Guillermo Rivera-Martinez
(74) *Attorney, Agent, or Firm* — Honigman Miller Schwartz and Cohn LLP

(57) ABSTRACT

An apparatus includes a baseboard, a grid, a first marker, and a second marker. The grid has a plurality of cells integrally formed with the baseboard. The first marker is integrally formed with the baseboard and intersects the grid at a first angle with respect to a reference line. The second marker is integrally formed with the baseboard and intersects the grid at a second angle with respect to the reference line. The first angle and the second angle are vertically opposite. The grid, the first marker, and the second marker are made of materials having luminescence characteristics that are different than an x-ray characteristic of a material of the baseboard.

26 Claims, 12 Drawing Sheets

(51) Int. Cl.
*A61B 6/04* (2006.01)
*A61B 6/08* (2006.01)
*A61B 6/12* (2006.01)
*A61B 6/00* (2006.01)
*A61B 8/08* (2006.01)

(52) U.S. Cl.
CPC .............. *A61B 6/12* (2013.01); *A61B 6/4405* (2013.01); *A61B 6/505* (2013.01); *A61B 8/0875* (2013.01)

(58) Field of Classification Search
CPC . G06T 2207/10121; G06T 2207/30004; G06T 2207/30052; G06T 2207/30204; G06T 2211/424
See application file for complete search history.

(56) References Cited

U.S. PATENT DOCUMENTS

| | | | |
|---|---|---|---|
| 2011/0191084 A1* | 8/2011 | Cooke | G06G 7/60 703/11 |
| 2013/0178863 A1* | 7/2013 | Kubiak | A61B 19/26 606/102 |
| 2014/0093154 A1* | 4/2014 | Penenberg | G06F 19/321 382/132 |

OTHER PUBLICATIONS van der Bom et al.,Pelvic Rotation and Tilt Can Cause Misinterpretation of the Acetabular Index Measured on Radiographs, Feb. 2011, Sringer,Clin Orthop Relat Res (2011) 469: pp. 1743-1749.*

* cited by examiner

IMAGING ALIGNMENT APPARATUS AND METHOD OF USE THEREFOR

CROSS REFERENCE TO RELATED APPLICATIONS

This U.S. patent application claims priority under 35 U.S.C. §119(e) to U.S. Provisional Application 61/722,471, filed on Nov. 5, 2012, the contents of which are hereby incorporated by reference.

TECHNICAL FIELD

This disclosure relates to an alignment apparatus and a method of use therefor.

BACKGROUND

Total hip replacement procedures are performed over 600,000 times every year worldwide and over 350,000 times a year in the United States. These procedures involve removing bone and cartilage from the diseased hip and replacing it with metal and plastic to give the patient a smooth, articulating, and long-lasting hip. Intra-operatively, the surgeon balances the unique bone anatomy of the patient with limited implant sizing and shaping variations made available by each device manufacturer. To optimize the performance of the hip, the surgeon balances the soft tissue envelope around the hip as well as the mechanical balance of the hip. Achieving this balance within a defined three-dimensional space drives the use of imaging devices, such as intra-operative C-arm x-rays.

An x-ray device outputs images of the patient's pelvic area, the surgeon begins evaluating the leg length, femoral offset, and cup inclination visually. A variation of even a small amount from an optimal position can change the stability, mechanical balance, and potentially the longevity of the hip replacement. Thus, the accuracy of the x-ray image and the analysis thereof are very important stages of the procedure.

SUMMARY

One aspect of the disclosure provides an apparatus including a baseboard, a grid, a first marker, and a second marker. The grid has a plurality of cells integrally formed with the baseboard. The first marker is integrally formed with the baseboard and intersects the grid at a first angle with respect to a reference line. The second marker is integrally formed with the baseboard and intersects the grid at a second angle with respect to the reference line. The first angle and the second angle are vertically opposite. The grid, the first marker, and the second marker are made of materials having luminescence characteristics that are different than an luminescence characteristic of a material of the baseboard.

Implementations of the disclosure may include one or more of the following features. In some implementations, the first marker and the second marker form a V-shape. Additionally or alternatively, the first marker and the second marker may intersect at a vertical axis of the baseboard.

In some examples, the materials of the grid, the first marker, and the second marker are denser than the material of the baseboard, and may be embedded within the baseboard. The apparatus may include a target disposed on the baseboard at a central axis of the baseboard. Additionally or alternatively, the first marker and the second marker may meet at the central axis. In some implementations, the baseboard and the grid share a central axis. The apparatus may include one or more manipulation devices coupled to an end of the baseboard. In some implementations, the one or more manipulation devices pivotally coupled to the end of the baseboard.

Another aspect of the disclosure provides a method for calibrating an imaging device over a patient. The method includes positioning the patient on a table, registering the imaging device with respect to a pelvis of the patient, placing an alignment apparatus over the pelvis of the patient, and registering the grid with respect to the pelvis using the imaging device. The alignment apparatus includes a baseboard and a grid formed integrally with the baseboard. The grid has different luminescence characteristics than those of the baseboard. In some examples, the method is iteratively performed until an amount of detectable cross-parallax is reduced to within a tolerance.

The method may include: a) capturing an image of the pelvis; b) determining whether a horizontal pelvic line of the pelvis is aligned with a horizontal axis of a field of view of the imaging device in the image, and c) when the horizontal pelvic line is not aligned, adjusting the position of the patient and/or a position of the imaging device. Steps a), b), and c) are iteratively performed until the horizontal pelvic line is aligned with the horizontal axis. Additionally or alternatively, the horizontal axis may be the center horizontal axis of the field of view. The horizontal pelvic line may be a transischial line of the pelvis.

In some examples, registering the imaging device includes: a) capturing an image of the pelvis; b) determining whether a symphysis pubis of the pelvis is aligned with a vertical axis of a field of view of the imaging device in the image, and c) when the symphysis pubis is not aligned with the vertical axis in the image, adjusting a position of the patient and/or a position of the imaging device. Steps a), b), and c) are iteratively performed until the symphysis pubis is aligned with the vertical axis. Additionally or alternatively, the horizontal axis may be the center vertical axis of the field of view.

In some implementations, registering the imaging device includes: a) capturing an image of the pelvis; b) determining whether a right obturator foramen of the pelvis and a left obturator foramen are substantially equal in size and shape in the image, and c) when the right obturator foramen and the left obturator foramen are not substantially equal in size and shape in the image, adjusting a position of the patient and/or a position of the imaging device. Steps a), b), and c) are iteratively performed until the right obturator foramen and the left obturator foramen are substantially equal in size and shape in the image.

In some examples, registering the imaging device includes: a) capturing an image of the pelvis; b) determining whether a right femur and a left femur are bilaterally symmetrical about a vertical pelvic line in the image, and c) when the right femur and the left femur are not bilaterally symmetrical about the vertical pelvic line of the pelvis in the image, adjusting a position of the left femur and/or the right femur. Steps a), b), and c) are iteratively performed until the right femur and the left femur are bilaterally symmetrical about the vertical pelvic line of the pelvis in the image. The right femur and the left femur are bilaterally symmetrical about the vertical pelvic line of the pelvis in the image when the right femur and the left femur are substantially parallel to one another and both are substantially perpendicular to a horizontal pelvic line of the pelvis in the image. Additionally or alternatively, the horizontal pelvic line may be a transischial line of the pelvis.

In some implementations, registering the imaging device includes: a) capturing an image of the pelvis; b) determining whether a right femur and a left femur are equally rotated in the image, and c) when the right femur and the left femur are not equally rotated, rotating the left femur and/or the right femur. Steps a), b), and c) are iteratively performed until the right femur and the left femur are equally rotated. Additionally or alternatively, steps a), b), and c) may be performed for both hips.

Registering the grid may include: a) capturing an image of the pelvis; b) determining whether a reference line of the grid is aligned with a horizontal pelvic line of the pelvis in the image, and c) when the reference line of the grid is not aligned with the horizontal pelvic line, adjusting a position of the alignment apparatus. Steps a), b), and c) are iteratively performed until the reference line is aligned with the horizontal pelvic line. Additionally or alternatively, the horizontal line may be a transischial line of the pelvis.

In some implementations, registering the grid may include: a) capturing an image of the pelvis; b) determining whether a target on a center vertical axis of the baseboard is aligned with a symphysis pubis of the pelvis in the image, and c) when the target is not aligned with the symphysis pubis, adjusting a position of the alignment apparatus. Steps a), b), and c) are iteratively performed until the reference line is aligned with the horizontal pelvic line. Additionally or alternatively, the horizontal pelvic line may be a transischial line of the pelvis.

In some examples, the method further includes: a) sliding the imaging device over a hip of the patient; b) capturing an image of the femur and the pelvis; c) determining whether a center of a femoral head is aligned with a center vertical axis of the field of view of the imaging device in the image, and d) when the center of the femoral head is not aligned with the center vertical axis of the field of view of the imaging device in the image, adjusting the position of the patient and/or the imaging device. Steps b), c), and d) are iteratively performed until the center of the femoral head is aligned with the center vertical axis of the field of view of the imaging device in the image.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
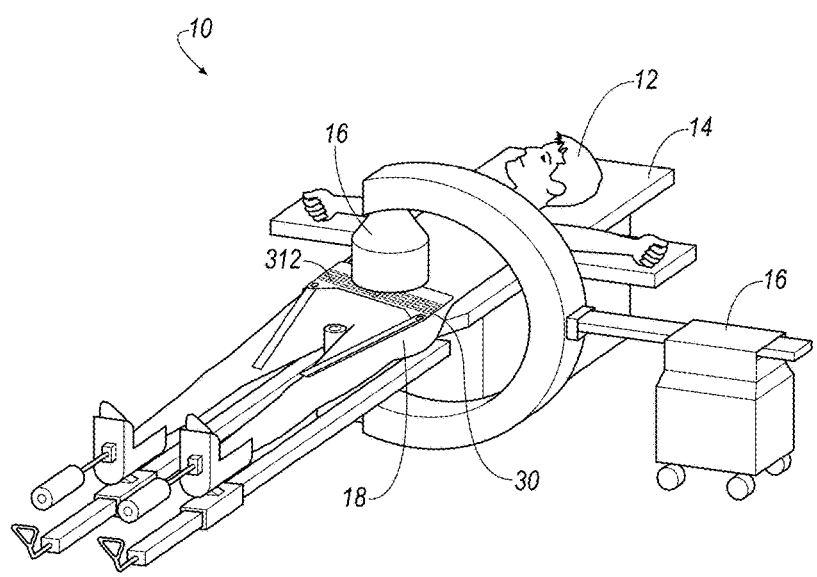
FIG. 1 illustrates a patient on an operating table.

FIG. 1 shows an example operating room environment 10. In the example of FIG. 1, a patient 12 is on an operating table 14 in a supine position. An imaging device 16 captures one or more images of a pelvic area/hip 18 of the patient 12. For instance, if the patient 12 is receiving a hip replacement surgery, the imaging device 16 captures images of the pelvic area/hip 18 of the patient 12 so that the surgeon performing the surgery can view internal images of this area during the operation. As shown, the imaging device 16 is a C-arm x-ray device. Any other suitable imaging device 16 may be used, however, such as a fluoroscope and the like. While this disclosure will reference imaging device 16 as a C-arm x-ray device, it is to be understood that the claimed device and methods should not be so limited to the exemplary C-arm unless specifically expressed. In the case of a C-arm x-ray device, the imaging device 16 may have a nine inch tube or a twelve inch tube, among other possibilities. In an implementation, the imaging device 16 may be connected to a display device (not shown), such that a user can command the imaging device 16 to capture an image. As used herein, the term "user" can refer to a surgeon, an x-ray technician, or any other personnel associated with the surgery. Upon receiving a command, the imaging device 16 captures an image and transmits the image to the display device. The display device can display the captured image.

Figure 2:
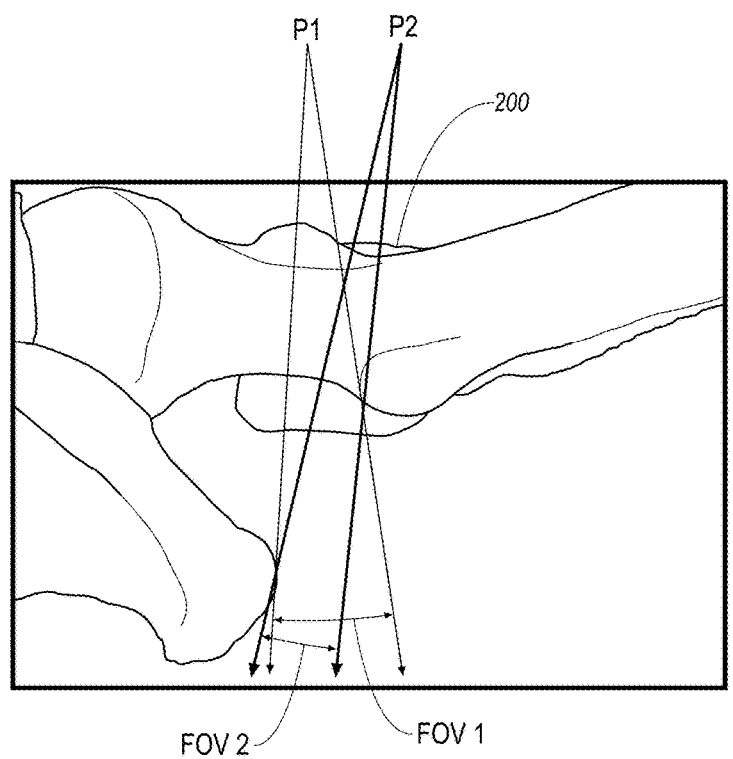
FIG. 2 illustrates an example of cross-parallax.

One issue that can arise when using an imaging device 16 is that when the imaging device 16 is repositioned at another location with respect to the patient 12, cross-parallax can occur and may thereby distort the spatial relationships between objects in the field of view of the imaging device 16. FIG. 2 illustrates an example of cross-parallax. Cross-parallax can refer to inconsistencies in images of an object 200 that result from viewing an object 200 from different viewing positions $P_1$, $P_2$. For instance, cross-parallax can refer to inconsistent distances between different parts of the hip and pelvis when viewed from different viewing angles. In the illustrated example, the imaging device 16 captures images from at least two positions and the drawings illustrate a first position, $P_1$, and a second position, $P_2$. As shown, the field of view $FOV_1$ of the imaging device 16 at the first position $P_1$ captures the object 200 at a different angle than the field of view $FOV_2$ of the imaging device 16 from the second position $P_2$. The foregoing situation can cause cross-parallax, which may hamper the surgeon's ability to accurately measure the pelvic offset, leg length, or cup inclination of the pelvis.

Referring back to FIG. 1, in an implementation, the patient 12 is placed upon the operating table 14 in a supine position. An alignment apparatus 30 is placed atop the patient 12 during surgery. In the illustrated embodiment, the alignment apparatus 30 is placed over the hips 18 of the patient 12. The alignment apparatus 30 can be used to align an imaging device 16 during or prior to performing an operation and/or to measure internal distances within the patient. As will be discussed in further detail below, the alignment apparatus 30 includes a grid 312 (FIG. 3) that is visible using the imaging device 16.

Figure 3A:
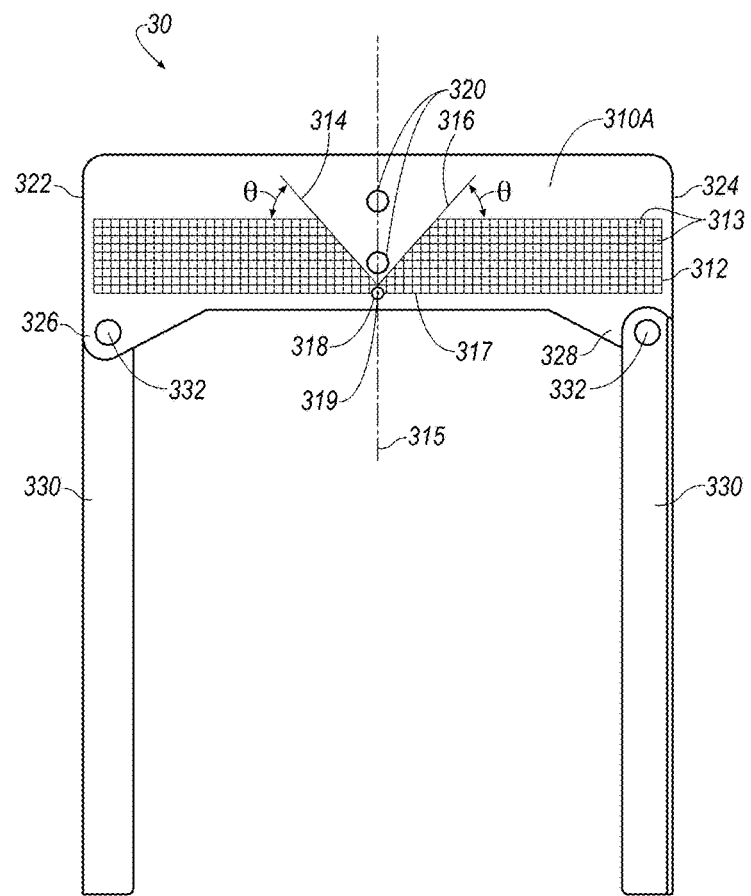
FIGS. 3A and 3B illustrate an example alignment apparatus.
Figure 3B:
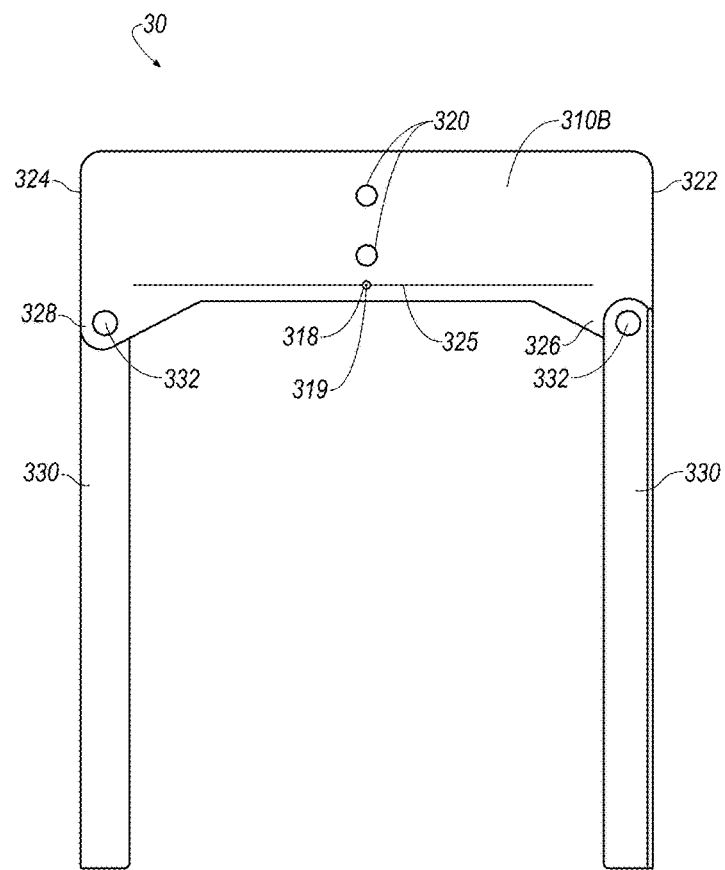

Referring now to FIGS. 3A and 3B, FIG. 3A is a front view of the exemplary alignment apparatus 30 and FIG. 3B is a back view of the alignment apparatus 30. The illustrated alignment apparatus 30 includes a baseboard 310 and one or more manipulation devices 330. The front 310A of the baseboard 310 can include a grid 312, a first marker 314, a second marker 316, and a target 318, and one or more locator apertures 320. The back 310B of the baseboard 310 can include an orientation line 325, and the target 318. The baseboard 310 can further define one or more locator apertures 320.

In some implementations, the baseboard 310 is made of any suitable material. For instance, the baseboard 310 can be made of plastic, lighter metals (e.g., aluminum), composites, or cardboard. In the illustrated examples, the baseboard 310 has a width extending from a first side 322 to a second side 324. In an implementation, the width of the baseboard 310 can range from 20 cm to 80 cm, and the height of the baseboard 310 can range from 5 cm to 30 cm. In an implementation, the baseboard 310 can be substantially rectangular. In some implementations, the lower second side 328 and the lower first side 326 extend from the main body of the baseboard 310. The baseboard 310 may further include a manipulation device. For example, the manipulation device may include one or more legs. As depicted, manipulation devices 330 may include a first leg 330 that extends from the lower first side 326 of baseboard 310 and a second leg 332 that extends from the lower second side 328 of baseboard 310. In an implementation and as depicted, the legs 330 may be pivotally attached to the baseboard 310 to allow the legs 330 to fold onto the baseboard 310 or be optimally positioned to manipulate the position of the baseboard 310 when on the patient. In the illustrated example, one or more attachment devices 332, such as pegs or the like, are provided to attach baseboard 310 to the legs 330, 332.

The grid 312, the first marker 314, and the second marker 316 can be integrally formed into or onto the front 310A of the baseboard 310. The grid 312, the first marker 314, and the second marker 316 can be made of one or more materials that have luminescence characteristics (e.g., x-ray characteristics) that are different than the luminescence characteristics (e.g., x-ray characteristics) of the baseboard 310. In some implementations, the grid 312, the first marker 314, and the second marker 316 are made of tungsten and/or barium sulfide. It is noted that the grid 312, the first marker 314, and the second marker 316 can be made of any other suitable materials having luminescence characteristics that sufficiently differ from the baseboard 310, such that the grid 312, the first marker 314, and the second marker 316 are visible in an image captured by the imaging device 16. For example, if the grid 312, the first marker 314, and the second marker 316 are made of a material that is sufficiently denser than the material of the baseboard 310, then the grid 312, the first marker 314, and the second marker 316 may appear more prominently in images output by the imaging device 16. Additionally or alternatively, the grid 312, the first marker 314, and the second marker 316 can display different characteristics if they are significantly thicker than the baseboard 310. In these implementations, if the grid 312, the first marker 314, and the second marker 316 are sufficiently thicker than the baseboard 310, the grid 312, the first marker 314, and the second marker 316 will appear more prominently in a captured x-ray image than the baseboard 310.

In an implementation, the grid 312 may be comprised of generally equal-sized cells 313. In some example, the cells 313 are five mm by five mm cells. While, equal-sized cells 313 are depicted, the cells 313 of the grid 312 do not need to be equally sized and can have other shapes, such as rectangles, diamonds, hexagons, or the like. The grid 312 includes a reference line 317. In the illustrated example, the reference line 317 is the horizontal line of the grid 312 closest to the target 318. The reference line 317 may be, however, any suitable horizontal line.

In the illustrated embodiment, the first marker 314 and the second marker 316 intersect the grid at an angle, θ. In an implementation, θ can be any suitable angle and preferably between 30 and 60 degrees. In some implementations, θ is approximately 45 degrees. In the illustrated example, the first marker 314 meets the second marker 316 at a center vertical axis 315 of the baseboard 310. In some implementations, the grid 312 may be discontinuous in an area between the first and second markers 314, 316, as shown in FIG. 3A. In other implementations, the grid 312 is continuous between the first and second markers 314, 316. In operation, the markers 314, 316 allow a surgeon to judge whether the cup inclination of a replacement hip is proper. For example, if an imaginary line tangentially connecting the acetabular shell of a hip implant is approximately equal to the angle of the first marker 314 or the second marker 316 (or within a certain range therefrom), then the surgeon may be able to conclude that the cup inclination is generally sufficient. Conversely, if the surgeon observes an angle of the imaginary line tangentially connecting the acetabular shell is less than the angle of the first marker 314 or the second marker 316 (or outside of a certain range therefrom), the surgeon may conclude that the cup inclination is not appropriate and work to remedy this arrangement. While only a first and second marker 314, 316 are depicted, some implementations may include additional markers (not shown) that extend towards the lateral edges of the baseboard 310 and the disclosure should not be so limited to the disclosed example.

In an implementation, the target 318 may be located at or near the intersection of the first and second markers 314, 316 and on the vertical axis 315. In some implementations, the target 318 extends through the baseboard 310. In other implementations, the target 318 is formed into the baseboard 310 or onto the baseboard 310. The target 318 is made of a material that has luminescence characteristics that are different than the luminescence characteristics of the baseboard 310. In some implementations, the target 318 includes a centrally located marker 319. The centrally located marker 319 is used for registering the grid 312 with respect to the patient's pelvis. The centrally located marker 319 can be, for example, a cylinder that extends the length of the target 318, a BB that is located inside the target 318, or a flat piece that is coupled to the end of the target 318. In some implementations, the centrally located marker 319 extends past the edge of the target 318. The centrally located marker 319 can be made of any suitable radio dense material having luminescence characteristics that are different than the target 318. The target 318, along with the grid 312 and the markers 314, 316, appear in the images captured by the imaging device 16.

In operation, the target 318 is used to assure that the grid 312 is orthogonal to the imaging device 16. The user can center the imaging device 16 over the grid 312. When images produced by the imaging device 12 show the target 318 aligned with a specific object and when the central marker 319 appears to be located centrally within the target 318, the user can determine that the imaging device 16 is orthogonal to the grid 312.

The locator apertures 320 may be located between the first marker 314 and the second marker 316 along the vertical axis 315 of the baseboard 310. In some implementations, the locator apertures 320 have a radius ranging from half a centimeter to two centimeters. The locator apertures 320 can be used to mark the patient 12 once the grid 312 has been registered with respect to the patient's pelvis. A user can draw a mark on the patient 12 or drapes covering the patient 12 through one or both of the locator apertures 320 such that if the alignment apparatus 30 is moved, the user can reposition the alignment apparatus 30 by locating the marks through the locator apertures 320.

In the illustrated example, the orientation line 325 is integrally formed into the back 310B of the baseboard 310. Alternatively or additionally, an orientation line 325 may be formed on the same side of the baseboard 310 as the grid 312. The orientation line 325 extends along a horizontal axis of the baseboard 310. In some implementations, the orientation line 325 is located along the same horizontal axis as the reference line 317. The orientation line 325 can be printed onto the baseboard 310. The orientation line 325 may or may not have luminescence characteristics that are different from the luminescence characteristics of the baseboard 310.

The orientation line 325 is used to position the baseboard 310 upon the patient 12 during a surgery. The imaging device 16 emits a light that indicates the center of the point of view thereof. In operation, when the imaging device 16 is extended or retracted, the user can confirm that the imaging device 16 and the grid 312 are aligned, if the laser light emitted by the imaging device 16 substantially remains on the line as the user extends or retracts the imaging device 16.

Figure 4A:
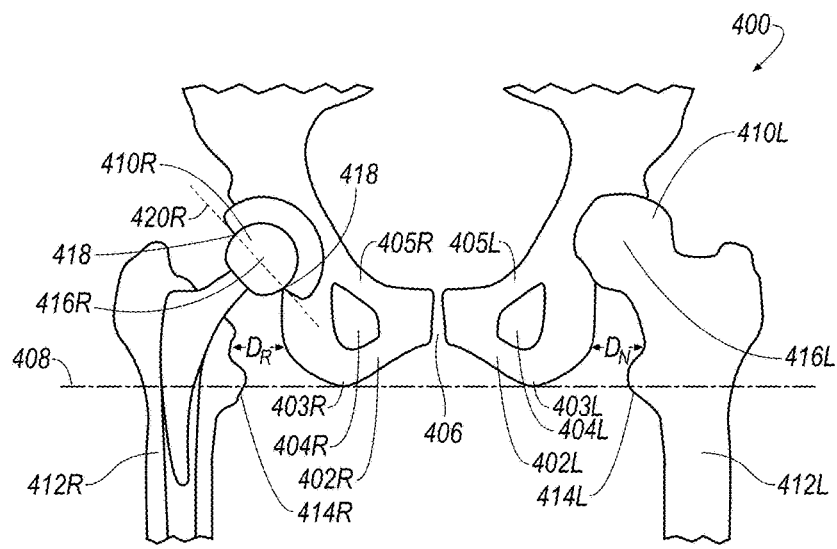
FIG. 4A illustrates an example pelvis of a human being.

FIG. 4A illustrates a pelvis 400. A pelvis includes, inter alia, a right ischium 402R, a left ischia 402L, a right obturator foramen 404R, a left obturator foramen 404L, a right pubis bone 405R, a left pubis bone 405L, and a symphysis pubis 406. The transischial line 408 is a horizontal line that extends tangentially from the lower portion 403L of the left ischia 402L to the lower portion 403R of the right ischium 402R. In the illustrated example, the left hip 410L is a natural hip and the right hip 410R is a replacement hip 410R. The hips 410R, 410L are coupled to the femurs 412R, 412L. The right femur 412R includes a right lesser trochanter 414R and a right femoral head 416R. The left femur 412L includes left lesser trochanter 414L and a left femoral head 416L.

When a hip replacement procedure is being performed, the surgeon has many objectives, including ensuring an appropriate cup inclination of the replacement hip 410R, an appropriate leg length of the replacement hip 410R, and an appropriate pelvic distance $PD_R$ of the femur 412R from the right ischium 402R. Referring to a right hip replacement, the pelvic distance $PD_R$ may be considered appropriate when it is approximately equal to the offset distance $PD_L$ of the femur 412L to the left ischium 402L. Similarly, a cup inclination of a replacement hip may be considered appropriate when the angle of the cup inclination line 420R tangentially intersecting the ends of the acetabular shell 418 is approximately equal to the angle of one of the markers 314 or 316. A leg length of a replacement hip may be considered appropriate when the rise from the outermost point of the lesser trochanter 414R to the outermost point of the corresponding ischium 402R is approximately equal to the rise from the outermost point of the lesser trochanter 414L on the side of the natural hip to the outermost point of the corresponding ischium 402L. The alignment apparatus 30 aids the surgeon in achieving these objectives.

Exemplary methods of using an alignment apparatus 30 will now be described, it being understood the variations to the method may be made without deviating from the inventive features disclosed herein. Accordingly, the scope of coverage conferred by the claims should not be limited to the described example.

Figure 4B:
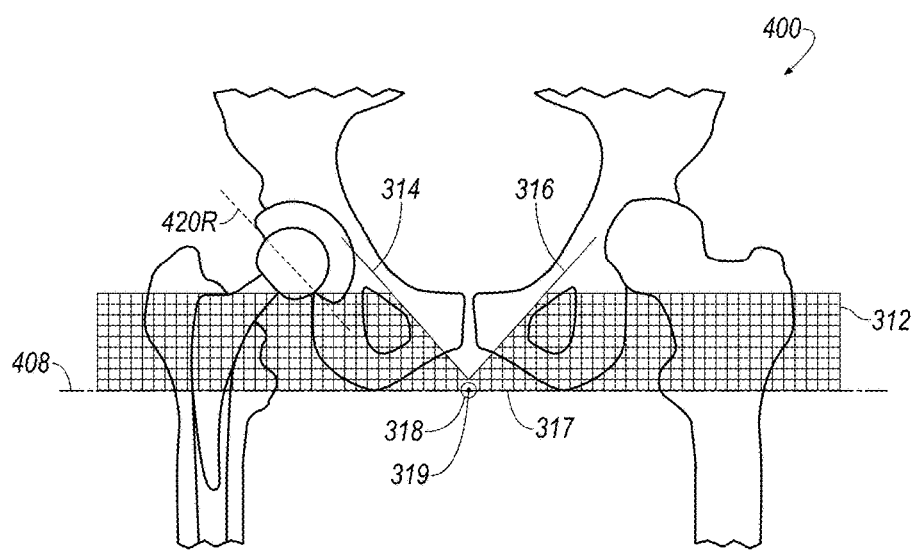
FIG. 4B illustrates the example pelvis with a grid laid thereupon.

FIG. 4B shows a grid 312 overlaid upon the pelvis 400. During an operation, the alignment apparatus 30 is overlaid upon the pelvis of the patient 12, such that the alignment apparatus 30 is located between the patient 12 and the imaging device 16. The imaging device 16 captures images of the pelvic area. Because the grid 312, the first marker 314, and the second marker 316 are made of materials having different luminescence characteristics (e.g., x-ray characteristics) than the baseboard 310, the image produced by the imaging device 16 includes the grid 312, the first marker 314, the second marker 316, and the target 318. The baseboard 310 is invisible or slightly visible. In an implementation, the surgeon aligns the grid 312, such that the markers 314 and 316 track the obturator foramens 404R, 404L, the ischia 402R, 402L, and/or the pubis bones 405R, 405L. In this way, the alignment apparatus 30 provides a frame of reference when measuring the pelvic distance, PD, of the replacement hip 410R. In particular, the surgeon or practitioner can count the number of cells 313 between the femur 412L and the corresponding ischium 402L. When setting a temporary hip, the surgeon can count the number of cells 313 between the femur 412R on the replacement hip side and the corresponding ischium 402R to ensure that an appropriate size hip is selected. Once the surgeon identifies an appropriate sized temporary replacement hip, the surgeon can select an appropriate sized permanent replacement hip and surgically implant the replacement hip 410R.

Figure 5:
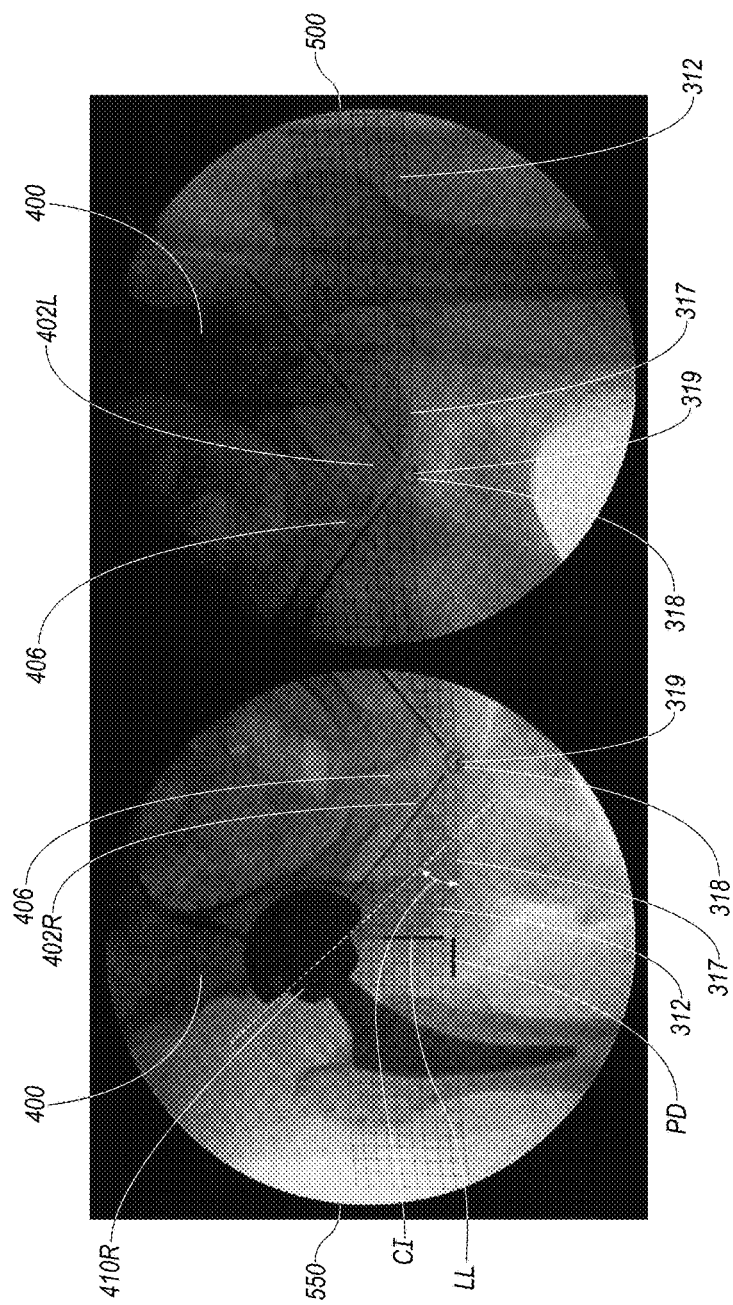
FIG. 5 illustrates example images captured by an imaging device.

FIG. 5 illustrates an example of the grid 312 in a first x-ray image 500 and a second x-ray image 550. The first image 500 shows the left side of the pelvis 400 with the grid 312 overlaid thereon. The second image 550 shows the right side of the pelvis 400 with the grid 312 overlaid thereon. In the second image a replacement hip 410R has been inserted into the patient 12.

As shown, the field of view of the imaging device 16 cannot capture the entire pelvis 400 of a patient 12. Thus, a user can position the grid 312 over the pelvis 400 of the patient 12. A user can manipulate the position of the grid 312 using the legs 330 of the apparatus 30. When the apparatus 30 is suitably aligned, the surgeon or practitioner can take measurements relating to the pelvis (e.g., pelvic distances PD, leg lengths LL, and cup inclination CI).

The user can reposition the imaging device 16 to capture a second image 550. The second image 550 shows a replacement hip 410R that has been inserted into the patient. The user can count the distance offset of the replacement hip 410R. In some scenarios, the grid 312 may require repositioning. In order to reduce cross-parallax, the user calibrates the imaging device 16 over the patient. Calibrating the imaging device 16 includes determining appropriate locations to position the imaging device 16 with respect to the patient and an appropriate location for the alignment apparatus 30 such that cross-parallax is reduced or eliminated.

Figure 6:
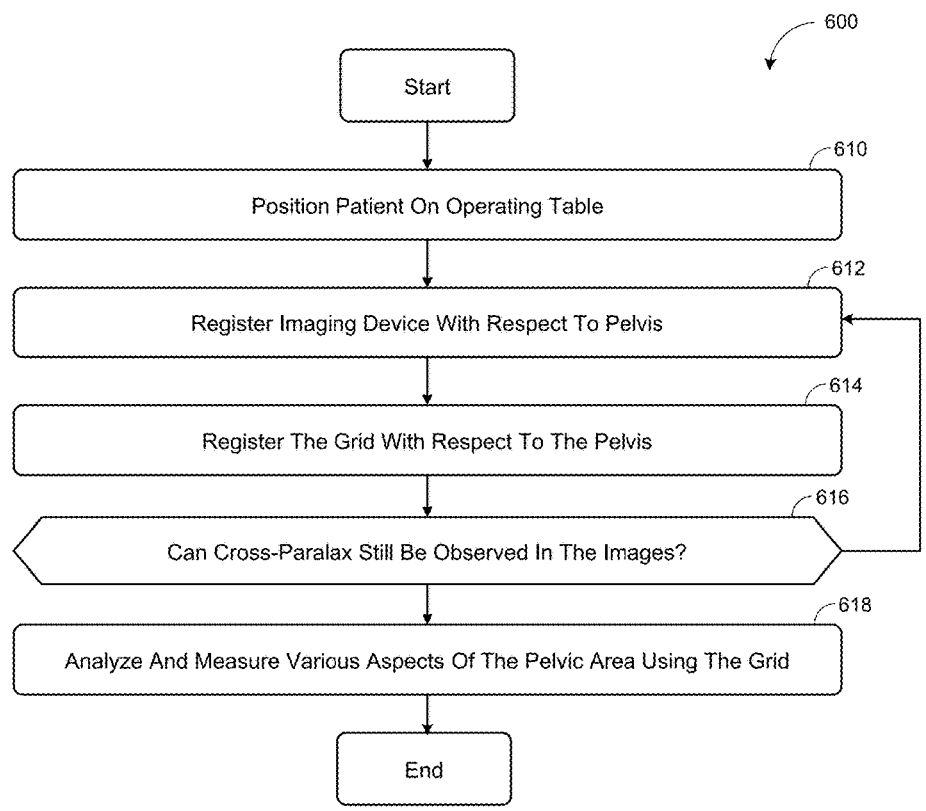
FIG. 6 illustrates an example method for calibrating an imaging device with respect to a patient.

Referring now to FIG. 6, an example method 600 for calibrating an imaging device 16 with respect to a patient 12 using an alignment apparatus 30 is shown. A user can perform the method 600 in the operating room during or prior to an operation (e.g., a hip replacement operation). While reference is a made to a single user, it is noted that the method 600 may be performed by multiple users or under the control of a single user.

At step 610, the patient 12 is placed on the operating table 14. For purposes of explanation, the patient 12 is positioned in the supine position. It is noted that for different procedures, the patient 12 may be placed in other positions.

At step 612, the user registers the imaging device 16 with respect to the patient 12. Registration of the imaging device 16 can refer to a process by which the user positions the imaging device 16 so that the field of view of the imaging device 16 includes specific markers inside of the patient's body at specific locations in the field of view of the imaging device 16.

Figure 7:
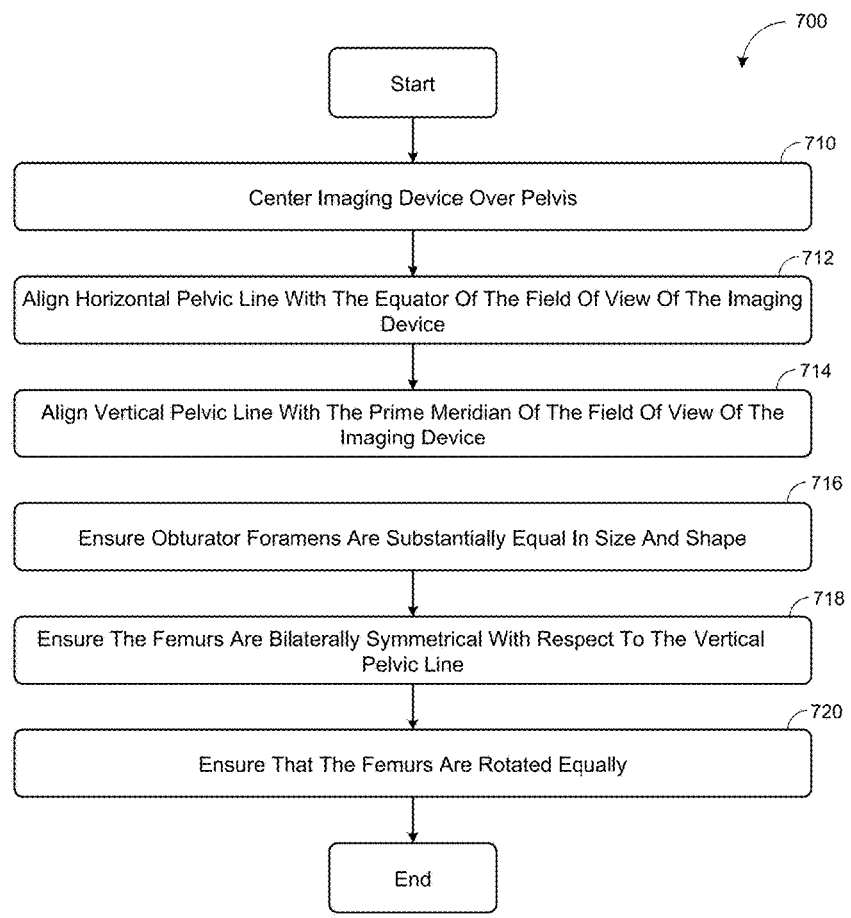
FIG. 7 illustrates an example method for registering an imaging device.
Figure 8:
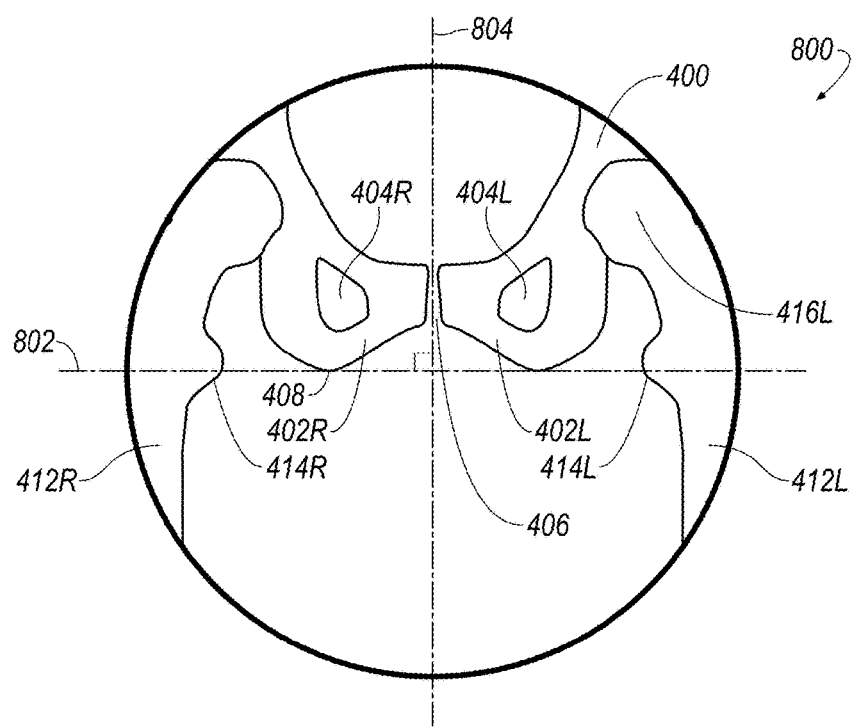
FIG. 8 illustrates an example field of view of an imaging device.

FIG. 7 illustrates an example method 700 for registering the imaging device 16 with respect to the patient 12. FIG. 8 illustrates an example field of view 800 of a registered image device 16. Reference is made to FIG. 8 to explain the method 700 of FIG. 7.

At step 710, a user centers the imaging device 16 over the pelvis 400. The user does not need to exactly center the imaging device 16 at this point, but the imaging device 16 should be over the central area of the pelvis 400.

At step 712, the user aligns a horizontal pelvic line (e.g., the transischial line 408) with the equator 802 of the field of view 800 of the imaging device 16. A horizontal pelvic line can refer to any line that extends horizontally or substantially horizontally across the pelvis 400, such as the transischial line, a line that connects the bottoms or the tops of the obturator foramens 404R, 404L of the pelvis 400, a line that connects the teardrops, or any other horizontal line that connects pelvic landmarks. For purposes of explanation, reference is made to the transischial line 408 and alignment can be performed with respect thereto. The equator 802 can refer to the central horizontal axis extending across the field of view 800 of the imaging device 16. This step may be an iterative process, whereby the user captures an image of the patient 12, checks the image to determine whether the transischial line 408 of the pelvis 400 is aligned with the equator 802 of the field of view 800. If not, the user can adjust the patient 12 and/or the imaging device 16 until the transischial line 408 is aligned with the equator 802. Further, while the equator 802 is used as an example, the user can align the transischial line 408 with other horizontal axes in the field of view 800 instead of the equator 802.

At step 714, the user aligns a vertical pelvic line (e.g., the symphysis pubis 406) with the prime meridian 804 of the field of view 800 of the imaging device 16. For purposes of explanation, alignment is described with respect to the symphysis pubis 406, as the symphysis pubis 406 is centrally located with respect to the pelvis 400. The prime meridian 804 can refer to the central vertical axis extending through the field of view 800 of the imaging device 16. Like the step of aligning the transischial line 408, this step may be an iterative process, whereby the user captures an image of the patient 12, checks the image to determine whether the symphysis pubis 406 is aligned with the prime meridian 804. If not, the user can adjust the patient 12 and/or the imaging device 16 until the symphysis pubis 406 is aligned with the prime meridian 804. Further, while the prime meridian 804 is used as an example, the user can align the symphysis pubis 406 with other vertical axes in the field of view 800.

At step 716, the user ensures that the right obturator foramen 404R and the left obturator foramen 404L appear as having similar shapes and sizes in the field of view 800 of the image device 16. This can be an iterative process, whereby the user can capture images and manipulate the patient 12 and/or the imaging device 16 until the right obturator foramen 404R and the left obturator foramen 404L appear to have substantially similar shapes and sizes in the captured image.

At step 718, the user ensures that the right femur 412R and the left femur 412L are substantially bilaterally symmetrical with respect to the horizontal pelvic line (e.g., transischial line 408). In some implementations, the user can substantially ensure that the right femur 412R and the left femur 412L are substantially parallel and that the femurs 412R, 412L are substantially perpendicular to the transischial line 408. This process is also iterative, whereby the user can capture images and manipulate (abduct and/or adduct) the legs of the patient 12 until the right femur 412R and the left femur 412L are parallel and perpendicular to the transischial line 408. Alternatively, the user can substantially ensure that the angles at which the central axes of the right femur 412R and the left femur 412L respectively intersect the transischial line 408 are at substantially the same angle.

At step 720, the user substantially ensures that the right femur 412R and the left femur 412L are rotated substantially equally. The user can iteratively capture images and rotate the right leg and/or the left leg of the patient 12 until the right lesser trochanter 414R and the left lesser trochanter 414L appear to have substantially similar sizes and shapes in the captured image.

As articulated above, the method 700 of FIG. 7 is provided for example. The ordering of the steps is not mandatory and the ordering of the steps can be varied without departing from the scope of the disclosure. Further, some or all of these steps may be performed at the same time. For instance, the user can adjust the imaging device 16, manipulate the pelvis 400, abduct the right femur 412R, and adduct the left femur 412L of the patient 12 before taking a subsequent image. In this way, the user may align the transischial line 408 and the symphysis pubis 406 with the equator 802 and the prime meridian 804, respectively between consecutive images.

Figure 9:
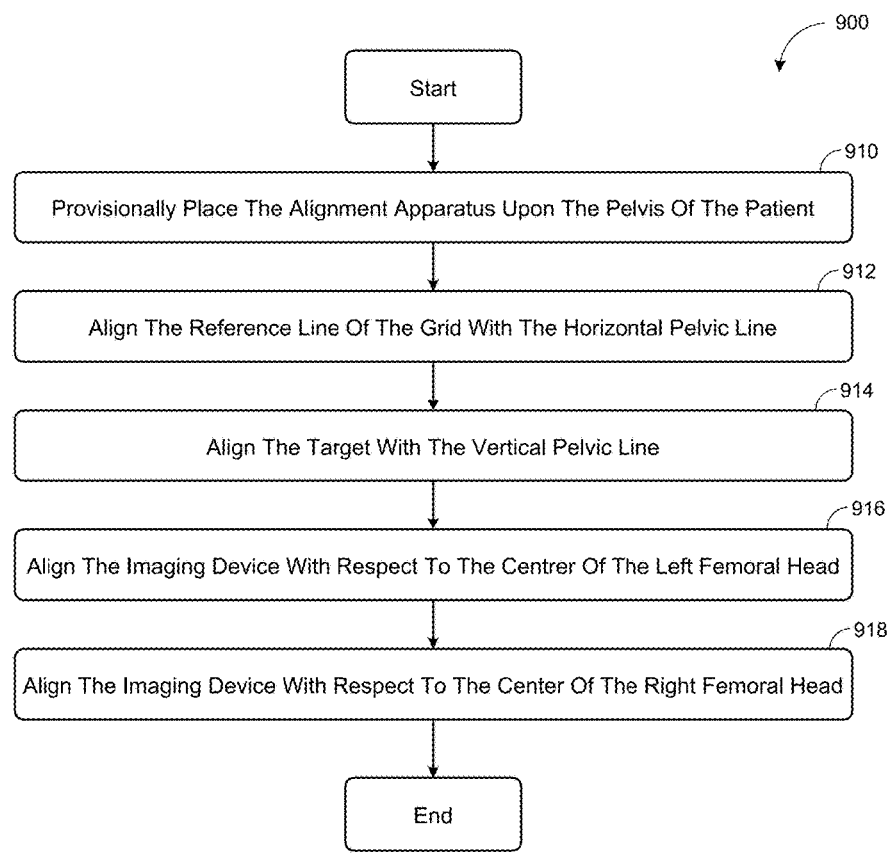
FIG. 9 illustrates a method for registering a grid with respect to a pelvis.
Figure 10:
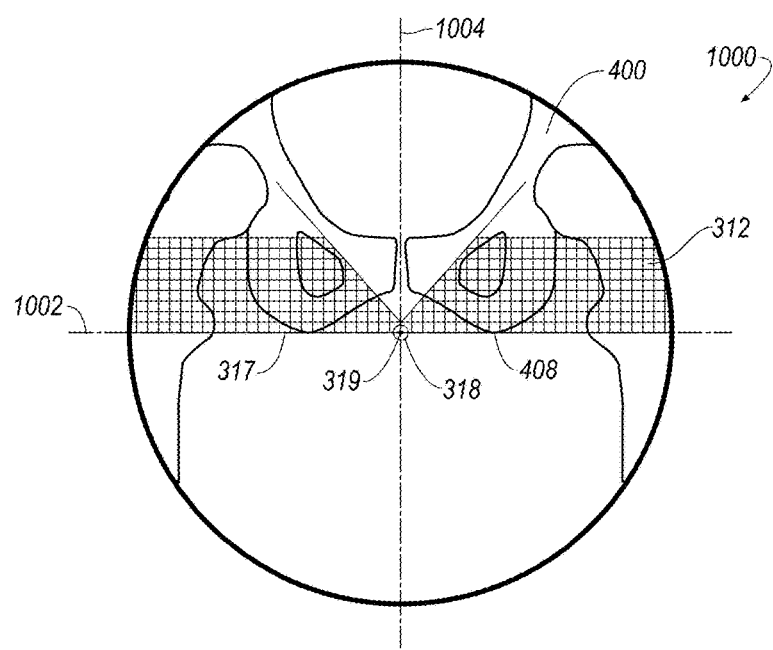
FIG. 10 illustrates an example field of view of an imaging device.
Figure 11:
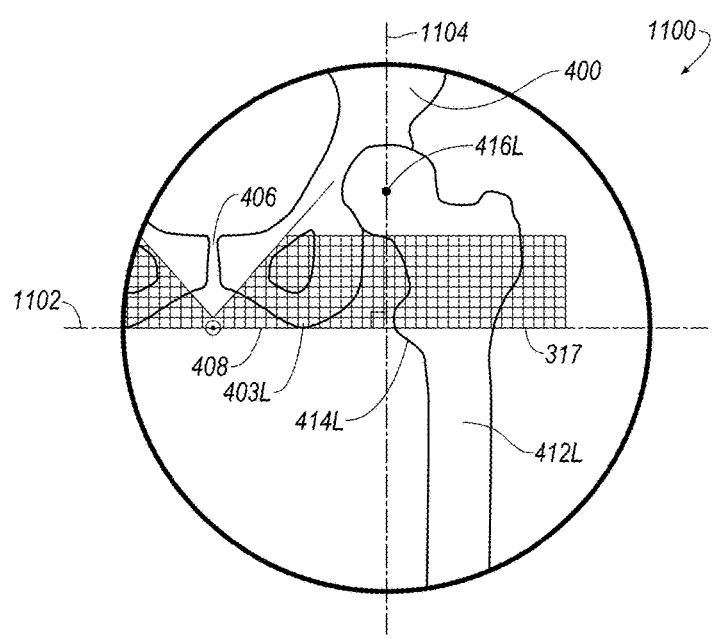
FIG. 11 illustrates an example field of view of an imaging device.

Referring back to FIG. 6, at step 612, the user registers the grid 312 with respect to the pelvis 400. FIG. 9 illustrates an example method 900 for registering the grid 312 with respect to the pelvis 400. FIG. 10 illustrates an example field of view 1000 where the imaging device 16 is positioned above the grid 312 and the pelvis 400 of the patient 12. FIG. 11 illustrates an example field of view 1100 where the imaging device 16 is positioned above the grid 312 and the left femur 412L of the patient. References are made to FIGS. 10 and 11 to describe the method 900 of FIG. 9.

At operation 910, the user provisionally places the alignment apparatus 30 on the pelvis 400 of the patient 12. The user can attempt to align the center of the grid 312 and the center of the pelvis 400. At operation 912, the user aligns the reference line 317 of the grid 312 with the horizontal pelvic line (e.g., the transischial line 408). The user can iteratively capture images of the pelvis 400 and adjust the positioning of the alignment apparatus 30 until the reference line 317 of the grid 312 is properly aligned with the transischial line 408. The user can use the legs 330 of the alignment apparatus 30 to adjust the positioning of the grid 312. It is noted that while the bottom reference line 317 of the grid 312 is used to align the grid 312, other horizontal reference lines can be used as well.

At operation 914, the user aligns the target 318 with the vertical pelvic line (e.g., the symphysis pubis 406). The user can iteratively capture images of the pelvis 400 and adjust the positioning of the grid 312 with respect to the pelvis 400 until the target 318 and the symphysis pubis 406 are in line. Further, the user can iteratively capture images and adjust the angle of the imaging device 16 until the central marker 319 appears to be centered within the target 318 in a captured image.

At operation 916, the user aligns the imaging device 16 with respect to the central axis of the left femoral head 416L (FIG. 11). The user telescopes the imaging device 16 to a location above the left hip area. The user can then iteratively capture images and position the imaging device 16 so that the left femoral head 416L is aligned with the prime meridian 1104 of the field of view 1100. At operation 918, the user aligns the imaging device 16 with respect to the central axis of the right femoral head 414R. The user can align the imaging device 16 in the manner described above.

The method 900 of FIG. 9 is provided for example. The ordering of the steps is not mandatory and the ordering of the steps can be varied without departing from the scope of the disclosure.

Referring back to FIG. 6, at step 614, the user determines whether the cross-parallax has been substantially eliminated. The user can capture an image of the right hip and telescope the imaging device 16 to location above the left hip and capture another image. If the reference line 317 of the grid 312 remains at or substantially at the transischial line 408, then the user can determine that the cross-parallax has been substantially eliminated and the method 600 is complete. If the reference moves outside of a tolerance (e.g., two or more cells 313) away from transischial line in one of the images, then a significant amount of cross-parallax still exists. In this scenario, the user can iterate back to the first step and can perform the method 600 again.

When cross-parallax has been substantially eliminated, the user can analyze and measure various aspects of the pelvic area using the grid 312. The user can measure the pelvic distances of the right side and left side of the pelvis 400. Additionally or alternatively, the user can measure the cup inclination of a replacement hip or the natural hip. Additionally or alternatively, the user can measure the leg length at the right side and left side of the pelvis 400.

The method 600 of FIG. 6 is provided for example. The method 600 may be performed multiple times during an operation. For instance, during a hip replacement operation, the method 600 may be performed prior to implanting the temporary hip and again prior to implanting the permanent replacement hip. Furthermore, the alignment apparatus 30 may be used to perform additional surgeries not explicitly discussed herein.

A number of implementations have been described. Nevertheless, it will be understood that various modifications may be made without departing from the spirit and scope of the disclosure. Accordingly, other implementations are within the scope of the following claims.

What is claimed is:

1. An apparatus comprising:
   a baseboard;
   a grid having a plurality of cells integrally formed with the baseboard;
   a first marker integrally formed with the baseboard and intersecting the grid at a first angle with respect to a reference line;
   a second marker integrally formed with the baseboard and intersecting the grid at a second angle with respect to the reference line, the first angle and the second angle being vertically opposite;
   one or more manipulation devices coupled to the baseboard,
   wherein the grid, the first marker, and the second marker are made of materials having luminescence characteristics that are different than luminescence characteristics of a material of the baseboard, and wherein each of the one or more manipulation devices is a leg pivotally coupled to the baseboard and extends laterally away from the baseboard to allow one or more manipulation devices to fold onto the baseboard or manipulate the position of the baseboard when on a patient.

2. The apparatus of claim 1, wherein the first marker and the second marker form a V-shape.

3. The apparatus of claim 2, wherein the first marker and the second marker intersect at a vertical axis of the baseboard.

4. The apparatus of claim 1, wherein the materials of the grid, the first marker, and the second marker are denser than the material of the baseboard.

5. The apparatus of claim 1, wherein the grid, the first marker, and second marker are embedded within the baseboard.

6. The apparatus of claim 1, further comprising a target disposed on the baseboard at a central axis of the baseboard.

7. The apparatus of claim 6, wherein the first marker and the second marker meet at the central axis.

8. The apparatus of claim 1, wherein the baseboard and the grid share a central axis.

9. A method for calibrating an imaging device with respect to a patient, the method comprising:
   positioning the patient on a table;
   registering the imaging device with respect to a pelvis of the patient;
   placing an alignment apparatus over the pelvis of the patient and between the patient and the imaging device, the alignment apparatus including a baseboard and a grid formed integrally with the baseboard, the grid having different luminescence characteristics than those of the baseboard, the alignment apparatus having one or more manipulation devices extending laterally away from the baseboard and defining a leg pivotally coupled to the baseboard to allow the one or more manipulation devices to fold onto the baseboard or manipulate the position of the baseboard when on a patient; and
   registering the grid with respect to the pelvis using the imaging device.

10. The method of claim 9, wherein the method is iteratively performed until an amount of detectable cross-parallax is reduced to within a tolerance.

11. The method of claim 9, wherein registering the imaging device includes:
   a) capturing an image of the pelvis; and
   b) determining whether a horizontal pelvic line of the pelvis is aligned with a horizontal axis of a field of view of the imaging device in the image; and
   c) when the horizontal pelvic line is not aligned with the horizontal axis in the image, adjusting a position of the patient and/or a position of the imaging device;
   wherein, a), b), and c) are iteratively performed until the horizontal pelvic line is aligned with the horizontal axis.

12. The method of claim 11, wherein the horizontal axis is the center horizontal axis of the field of view.

13. The method of claim 11, wherein the horizontal pelvic line is a transischial line of the pelvis.

14. The method of claim 9, wherein registering the imaging device includes:
   a) capturing an image of the pelvis; and
   b) determining whether a symphysis pubis of the pelvis is aligned with a vertical axis of a field of view of the imaging device in the image; and c) when the symphysis pubis is not aligned with the vertical axis in the image, adjusting a position of the patient and/or a position of the imaging device, wherein, a), b), and c) are iteratively performed until the symphysis pubis is aligned with the vertical axis.

15. The method of claim 14, wherein the vertical axis is the center vertical axis of the field of view.

16. The method of claim 9, wherein registering the imaging device includes:

a) capturing an image of the pelvis; and b) determining whether a right obturator foramen of the pelvis and a left obturator foramen are substantially equal in size and shape in the image; and c) when the right obturator foramen and the left obturator foramen are not substantially equal in size and shape in the image, adjusting a position of the patient and/or a position of the imaging device;

wherein, a), b), and c) are iteratively performed until the right obturator foramen and the left obturator foramen are substantially equal in size and shape in the image.

17. The method of claim 9, wherein registering the imaging device includes:

a) capturing an image of the pelvis; and b) determining whether a right femur and a left femur are bilaterally symmetrical about a vertical pelvic line in the image;

c) when the right femur and the left femur are not bilaterally symmetrical about the vertical pelvic line of the pelvis in the image, adjusting a position of the left femur and/or the right femur;

wherein, a), b), and c) are iteratively performed until the right femur and the left are bilaterally symmetrical about the vertical pelvic line of the pelvis in the image.

18. The method of claim 17, wherein the right femur and left femur are bilaterally symmetrical about the vertical pelvic line of the pelvis in the image when the right femur and the left femur are substantially parallel to one another and both are substantially perpendicular to a horizontal pelvic line of the pelvis in the image.

19. The method of 17, wherein the horizontal pelvic line is a transischial line of the pelvis.

20. The method of claim 9, wherein registering the imaging device includes:

a) capturing an image of the pelvis; and b) determining whether a right femur and a left femur are equally rotated in the image; and c) when the right femur and the left femur are not equally rotated, rotating the left femur and/or the right femur;

wherein, a), b), and c) are iteratively performed until the right femur and the left femur are equally rotated.

21. The method of claim 9, wherein registering the grid includes:

a) capturing an image of the pelvis; and b) determining whether a reference line of the grid is aligned with a horizontal pelvic line of the pelvis in the image; and c) when the reference line of the grid is not aligned with the horizontal pelvic line, adjusting a position of the alignment apparatus;

wherein, a), b), and c) are iteratively performed until the reference line is aligned with the horizontal pelvic line.

22. The method of 21, wherein the horizontal pelvic line is a transischial line of the pelvis.

23. The method of claim 9, wherein registering the grid includes:

a) capturing an image of the pelvis; and b) determining whether a target on a center vertical axis of the baseboard is aligned with a symphysis pubis of the pelvis in the image;

c) determining whether a central maker appears in a center of the target in the image; and d) when the target is not aligned with the symphysis pubis or the central marker does not appear in the center of the target, adjusting a position of the alignment apparatus;

wherein, a), b), c), and d) are iteratively performed until the target is aligned with the symphysis pubis and the central marker appears in the center of the target in the image.

24. The method of 23, wherein the horizontal pelvic line is a transischial line of the pelvis.

25. The method of claim 9, further comprising:

a) telescoping the imaging device to a location above a hip of the patient;

b) capturing an image of the femur and the pelvis;

c) determining whether a center of a femoral head is aligned with a center vertical axis of the field of view of the imaging device in the image; and d) when the center of the femoral head is not aligned with the center vertical axis of the field of view of the imaging device in the image, adjusting the position of the patient and/or the imaging device;

wherein, b), c), and d) are iteratively performed until the center of the femoral head is aligned with the center vertical axis of the field of view of the imaging device in the image.

26. The method of claim 25, wherein a), b), c), and d) are performed for both hips.

* * * * *